United States Patent
Fischer et al.

(10) Patent No.: US 10,201,504 B2
(45) Date of Patent: Feb. 12, 2019

(54) SOLID DRUG STORAGE APPARATUS, FORMULATIONS AND METHODS OF USE

(71) Applicant: InCube Labs, LLC, San Jose, CA (US)

(72) Inventors: Elmar Fischer, San Jose, CA (US); Paul Spehr, San Jose, CA (US)

(73) Assignee: InCube Labs, LLC, San Jose, CA (US)

( * ) Notice: Subject to any disclaimer, the term of this patent is extended or adjusted under 35 U.S.C. 154(b) by 0 days.

(21) Appl. No.: 15/883,471

(22) Filed: Jan. 30, 2018

(65) Prior Publication Data

US 2018/0153816 A1    Jun. 7, 2018

Related U.S. Application Data

(63) Continuation of application No. 15/392,822, filed on Dec. 28, 2016, now Pat. No. 9,913,804.

(60) Provisional application No. 62/274,046, filed on Dec. 31, 2015.

(51) Int. Cl.
| | |
|---|---|
| B65D 83/02 | (2006.01) |
| A61K 9/48 | (2006.01) |
| B65B 1/04 | (2006.01) |
| A61K 31/635 | (2006.01) |
| A61K 9/14 | (2006.01) |
| B65D 59/04 | (2006.01) |
| B65B 5/04 | (2006.01) |
| B65B 7/28 | (2006.01) |

(52) U.S. Cl.
CPC .............. *A61K 9/48* (2013.01); *A61K 9/14* (2013.01); *A61K 31/635* (2013.01); *B65B 1/04* (2013.01); *B65B 5/04* (2013.01); *B65B 7/28* (2013.01); *B65D 59/04* (2013.01)

(58) Field of Classification Search
USPC ................... 206/530, 528; 53/471, 472, 454
See application file for complete search history.

(56) References Cited

U.S. PATENT DOCUMENTS

| | | |
|---|---|---|
| 3,367,484 A | 2/1968 | Nelson |
| 3,844,407 A | 10/1974 | Buie |
| 4,601,896 A | 7/1986 | Nugent |
| 5,443,461 A | 8/1995 | Atkinson |
| 6,336,904 B1 | 1/2002 | Nikolchev |
| 6,443,307 B1 | 9/2002 | Burridge |
| 7,815,929 B2 | 10/2010 | Muni |
| 8,425,474 B2 | 4/2013 | Glassman |

(Continued)

*Primary Examiner* — Jacob K Ackun
(74) *Attorney, Agent, or Firm* — Mahamedi IP Law LLP; Joel Harris

(57) ABSTRACT

Embodiments of the invention provide drug packaging and methods for producing drug packaging which can be sealed at room temperature and/or without the need for elevated temperatures above room temperature. Many embodiments provide drug packaging comprising pierceable tubing having a capsule shape (also referred to herein as a pierceable capsule and/or pierceable drug capsule) containing a solid drug such as a drug pellet and methods for producing pierceable drug capsules which can be sealed at room temperature. Embodiments are particularly useful for the packaging and delivery of drugs used in implantable drug delivery devices as well as packaging of drugs that are easily thermally degraded.

21 Claims, 5 Drawing Sheets

(56) References Cited

U.S. PATENT DOCUMENTS

| | | | |
|---|---|---|---|
| 2003/0039777 A1* | 2/2003 | Dalton | A61K 9/0092 428/35.7 |
| 2011/0251582 A1* | 10/2011 | Lennox | A61L 29/085 604/500 |
| 2011/0284583 A1 | 11/2011 | Fazzolari | |
| 2011/0313348 A1* | 12/2011 | Potter | A61M 5/30 604/60 |
| 2013/0129824 A1* | 5/2013 | Daniel | A61K 9/0034 424/465 |
| 2015/0032088 A1 | 1/2015 | Grattoni | |

* cited by examiner

SOLID DRUG STORAGE APPARATUS, FORMULATIONS AND METHODS OF USE

RELATED APPLICATIONS

This application is a continuation of U.S. patent application Ser. No. 15/392,822, filed Dec. 28, 2016, which application claims the benefit of priority of Provisional U.S. Patent Application Ser. No. 62/274,046, entitled "Solid Drug Storage Apparatus, Formulations and Methods of Use", filed Dec. 31, 2015; the aforementioned priority applications being hereby incorporated by reference in their entirety.

FIELD OF THE INVENTION

Embodiments described herein relate to medication packaging. More specifically, embodiments described herein relate to a drug storage capsule which can be sealed at room temperature.

BACKGROUND

Many kinds of pharmacological drugs can be stably stored over a long period of time if stored dry at body temperature. Drugs may be stored in different kinds of packages.

Long term implantable devices dispensing drug doses on demand from small, sealed, pierceable capsules are known. These capsules must be easily pierced so that the drug may be transported from the drug storage device through a catheter lumen to a location in the body where the drug may be delivered for therapy.

Various forms of packaging for solid form drugs and other medically related products (e.g. glucose monitoring strips, contacts lenses, etc.) require that sealing be done at high temperature. This process is cumbersome, costly and risks a compromised seal if the process is not performed at a required temperature. A poorly sealed product can in turn compromise the storage life, activity and/or functionality of the drug or other component to be sealed. Furthermore, the use of elevated temperatures during the sealing process can thermally degrade the contents of the package, such as the drug or diagnostic test strip. Thus, there is a need for an improved packaging for drugs and other medically related products which can be sealed without utilizing elevated temperatures.

BRIEF SUMMARY

Embodiments of the invention provide for a sealed package to store a dose of medication. The package can be sealed at room temperature and/or without the need for elevated temperatures above room temperature. The package includes at least one portion covered by a breakable membrane. The dose can be released by breaking the membrane.

In an embodiment, a hermetically sealed package assembly stores a dose of medication to be delivered via an implantable device. The package assembly is formed by two joined tubular sections, at least one of the sections having a foil-covered end which can be pierced to remove the medication dose. Prior to the joining of the tubular sections, the foil may be bonded to one of the tubular sections by use of a high temperature compliant material.

Many embodiments provide a drug storage package comprising a pierceable tubing having a capsule shape (also referred to herein as a pierceable capsule and/or a pierceable drug capsule) containing a solid drug (e.g., a drug pellet). Particular embodiments provide for a drug packaging comprising a capsule formed from two joined sections of tubing. The sections are joined by sliding the sections together in an interference fit or other related manner. The packaging can be sealed at room temperature. The capsule may be structured to contain a solid drug element such as a drug pellet.

One embodiment provides a method for the fabrication of pierceable packaging for solid drug medication elements. Such elements include pellets, tablets and the like. The medication elements may comprise one or more therapeutic agents which lose their bioactivity when exposed to an elevated temperature. In an embodiment, the method of fabrication comprises sliding a first larger diameter tube having a covered end and an open opposite end over a first open end of a second smaller diameter tube, the second tube having a flared covered end opposite the open end. Each tube has a lumen through which a medication element may pass. Each of the respective coverings over the tubing ends comprises a pierceable material that is pierceable by a pin or other sharp object. In implementations, the medication element is positioned within the lumen of either the first or second tube. The first tube is advanced over the flared end of the second tube to create a seal between the first tube and second tube by an interference fit between the tubes. The seal created between the first and second tubes may be hermetic. In embodiments, the seal is created by the interference fit alone, without the need for elevated temperature to form the seal. The joined first and second tubes comprise a packaging assembly, wherein the medication element is sealed in the packaging assembly while substantially preserving the bioactivity of the therapeutic agent (e.g. with respect to the bioactivity of the agent as prior to the sealing process). In particular embodiments, at least about 90%, and more preferably at least about 95% and still more preferably at least about 99% of the bioactivity of the drug is preserved after the sealing process. The medication element is accessible while within, or removable from, the packaging assembly by employment of a piercing process for at least one of the covered tubing ends.

In particular embodiments, the drug capsules can be configured to be stored or otherwise placed in an implantable drug delivery device configured to deliver the medication element within the capsule to a selected delivery site such as the heart, brain, GI organ, vein, artery and the like. In these and other embodiments, the drug capsule can be configured to be engaged by a mechanism or the like which pierces the drug capsule and advances the medication element out of the capsule and to a selected delivery site in the body. According to one or more embodiments, the mechanism may include a piercing and advancement means which both pierces the capsule and advances the medication element out of the capsule to the selected delivery site. In particular embodiments, the piercing and advancement means may correspond to one or more of a metal wire, plastic tube and the like. It may also correspond to the use of a hydraulic or pneumatic pressure and/or pressure delivering device which is configured to provide hydraulic and/or pneumatic pressure which pierces the capsule and advances the medication element out of the capsule.

According to one or more embodiments, the solid form medication is formulated into pellets, though other solid formulations and shapes are also contemplated (e.g., tablets, spheres, powder, nanoparticles, etc.). Each pellet contains a selected dose of a drug or other therapeutic agent to treat a particular medical condition(s) such as epilepsy, arrhythmia or diabetes. The dose can be selected based on the patient's weight, age and particular condition including severity of the condition (e.g., moderate vs. severe arrhythmia). Also, the medication pellets are desirably formulated using one or more pharmaceutical excipients, including disintegrants so as disintegrate and dissolve the pellets in a controlled fashion to achieve and maintain a sufficient concentration of the drug (either at the tissue site, plasma or other tissue location) for treatment of the condition. The pellets are also desirably fabricated so as to have a shelf life of years or longer in vivo so the drug maintains its potency and therapeutic effectiveness. The pellets can include a plurality of drugs for treatment of conditions, for example, a cocktail of antiviral drugs for treatment of HIV AIDS.

After removal from the drug capsule (for example, by means of an advanceable wire or other piercing means), the pellets or other solid form of the medication can be delivered by a delivery mechanism to a delivery site such as subcutaneous tissue where they are configured to be broken down, disintegrated and absorbed by body tissue fluids so as to produce a desired concentration of the drug at a target tissue site. In some applications, the delivery site can be the same as the target site, such as the brain. In other applications, the target site can be different from the delivery site, for example, the delivery site can be intramuscular tissue in the chest and the target site can be the heart or the liver. The delivery site can be adjacent to the target site, for example adipose to deliver to underlying muscle tissue, or the medication can be placed at a non-oppositional site, for example, intramuscular delivery to reach the site of the heart. In each case, the medication pellet can include a selected dose of drug and be configured to disintegrate and be dissolved by body tissue fluids so as to yield a therapeutically effective concentration of the drug at the target tissue site. In many applications, this involves the pellet being dissolved by body tissue fluids at the delivery site (e.g., interstitial fluids) where the drug then diffuses from the tissue into the blood stream where it is carried to the target tissue site. Accordingly, in these and other applications, the dose of the drug in the pellet can be titrated to achieve a selected plasma (or other tissue compartment) concentration of the drug (or concentration range) for a selected period during and after dissolution of the pellet.

In some embodiments, the pellet (including the drug dose) is configured to disintegrate and be dissolved by the tissue fluids within a body compartment such as the cerebrospinal fluid (CSF) in the brain so as to achieve a selected concentration in the tissue fluid within that compartment. In particular embodiments for treating various neural disorders such as epileptic and other seizures, the pellet is configured to rapidly disintegrate and be dissolved in the CSF so as to rapidly achieve a selected concentration of the drug throughout the CSF bathing the brain to prevent the occurrence of the seizure or lessen its duration and severity. This can be achieved through the use of one or more super disintegrants as well as disintegrating enhancing features (e.g., pores, cracks or other intrusions) in or on the pellet. It can also be achieved by treating the pellet prior or after delivery with mechanical, electromagnetic, acoustical or other energy to weaken the pellet structure, create cracks and other structural defects for the ingress of fluids or initiate the breakup of the pellet into smaller pieces. In other embodiments, a solid form medication for delivery within the body of a patient is provided, the medication comprising at least one drug for the treatment of a disease or condition, wherein the medication has a shape and material properties so as to be: (i) be sealed in an embodiment of the drug capsule described herein that is stored in a container implanted within the body for an extended period without substantial degradation or deleterious effect to the medication, (ii) delivered to a delivery site, and (iii) dissolve in tissue fluids at the delivery site to produce a therapeutic effect at a target tissue site to treat the disease or condition.

As described herein, embodiments of the invention are particularly useful for the storage and delivery of drugs or therapeutic agents in an implanted drug delivery device including the long term storage of drugs in hermetically sealed packaging as well as the packing of drugs that easily thermally degraded. Further details of these and other embodiments and aspects of the invention are described more fully below, with reference to the attached drawing figures.

DETAILED DESCRIPTION OF THE INVENTION

Embodiments of the invention provide drug packaging and methods for producing drug packaging which can be sealed without the need for elevated temperatures above room temperature. Such embodiments allow for the sealing, hermetically or otherwise, of a medical element containing a drug or other therapeutic agent without loss of bioactivity of the drug due to thermal degradation. Preferably, though not necessarily, the packaging can be sealed within about 10° C. of room temperature (e.g., 30° C.), and more preferably within the range of normal room temperatures (typically in a range of about 20 to about 26° C., with particular embodiments of 21, 22, 23, 24 and 25° C.). Many embodiments provide drug packaging comprising a pierceable tubing containing a solid drug such as a drug pellet and methods for producing pierceable drug capsules which can be sealed at room temperature (e.g., about 20 to about 26° C. Particular embodiments provide drug packaging comprising an assembly with the appearance of a pierceable capsule (also referred to herein as a pierceable drug capsule) which is configured to store a solid drug element such as a drug pellet, and which can be sealed at room temperature (e.g., about 20 to about 26°) and/or without the use of elevated temperatures. The capsule is formed from two sections of tubing which are joined by sliding sections of the tubing together in an interference fit or other related manner. As used herein the term "about" means within +/−10% of a stated value for a dimension, characteristic, physical property and the like.

Figure 1A:
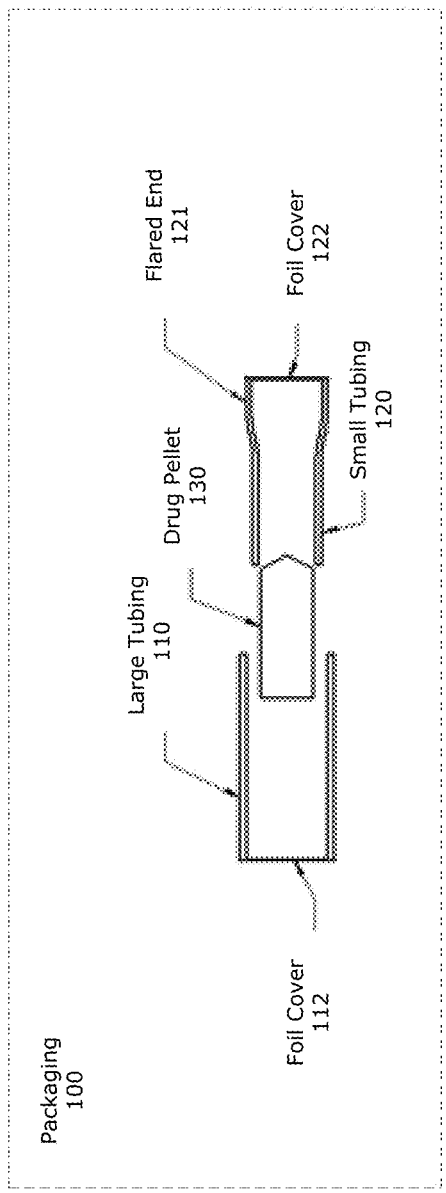
FIG. 1A illustrates a cross-sectional view of an embodiment of a capsule drug package of the present invention prior to assembly.

An embodiment of the capsule of the present invention will now be described. FIG. 1A illustrates a cross-sectional view of an embodiment of a capsule drug package of the present invention prior to assembly. A pierceable membrane (foil cover 112) is attached to a capsule body (large tubing 110). Another capsule body (small tubing 120) having a slightly smaller diameter than large tubing 110 is configured to be slideably inserted into an uncovered opening of large tubing 110 to form an interference fit. Small tubing 120 has a flared end 121 over a predetermined length, and the opening of small tubing 120 facing away from large tubing 110 is covered by another pierceable membrane (foil cover 122). Drug pellet 130 is positioned within the large tubing 110 and small tubing 120 to be held in storage. When foil cover 112 or foil cover 122 is broken, drug pellet 130 is released for delivery. While the embodiment of FIG. 1 illustrates a drug packaging having a capsule shape, it should be appreciated that embodiments of the invention contemplate many other shapes for example without limitation, cylindrical, spherical, cubical, rectangular and the like.

The pierceable membranes may correspond to a very thin foil of platinum, gold or other biocompatible metals materials, e.g., titanium, tantalum or stainless steel. Foil covers 112 and 122 may be constructed from similar or different materials. In various embodiments the thickness of foil covers 112 and 122 can vary from around 0.0001 to about 0.05" with specific embodiments of 0.0005, 0.001, 0.005, 0.005, 0.01, 0.025, and 0.04. As indicated below, the thickness may be selected to achieve a particular push out force. In an additional or alternative embodiments either foil covers 112 and 122 and/or other tubing 110 and 120 may coated with a material which colormetrically reacts (e.g., changes color with exposure to oxygen) so as to indicate if the hermetic seal of the drug packaging (including e.g., foil covers 112 and 122, tubings 110 and 120) has been compromised. Such coatings may include various iron containing compounds (e.g., various ferrous and ferric compounds) which turn red upon reaction with oxygen. In use such coatings allow for the determination if the seal of the packaging has been compromised either by visual inspection, machine vision and/or optical sensing such as various reflection and absorbance measurement methods known in the art. This in turn can allow a seal compromised packaging to be readily identified so as to not be loaded into an implanted drug delivery device which delivers the medication element to a patient (e.g., an implanted drug delivery device described herein) or even it was loaded into the implanted devices to not be delivered to the patient by the device.

In implementations the pierceable membrane may be configured to withstand various forces (e.g., internal bodily forces) so that the contents are not unintentionally removed. For example, in various embodiments the pierceable membranes may be configured to have a push out force in a range of about 0.2 to about 1 lbs with specific embodiments of at least about 0.2, 0.3, 0.4, 0.41, 0.5, 0.6, or 0.7 pounds of force with larger amounts contemplated. Push out force being the force required to push the pierce or break the membrane from the inside surface. The particular amount of push out force can be achieved by selection of one or more of the thickness, material selection or material processing (e.g. annealing or other thermal processing, coating etc.) used for the pierceable membrane.

According to various embodiments, the capsule body may correspond to a small tube fabricated from various biocompatible materials known in the art including various biocompatible metals such as stainless steel, titanium, tantalum and MP35N. Various polymeric materials are also considered for use in the membrane such as various polyimides, polyamides, PETs and other like materials and copolymers thereof.

Figure 1B:
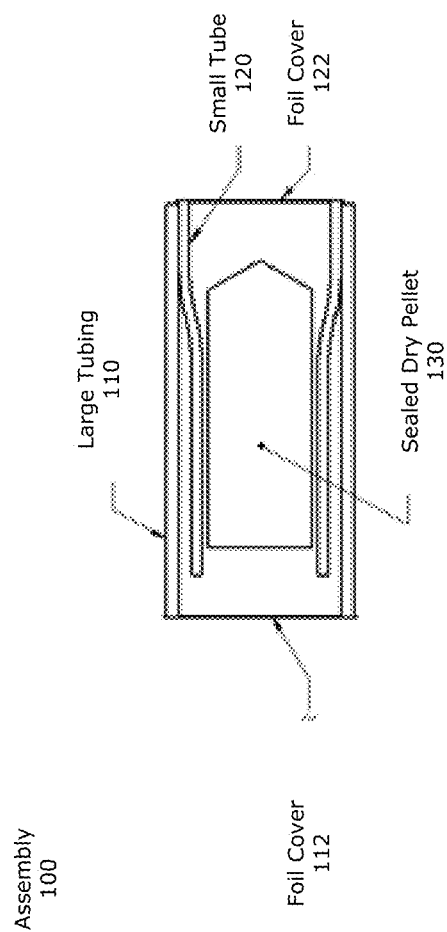
FIG. 1B illustrates a cross-sectional view of an embodiment of a capsule drug package of the present invention after assembly.

FIG. 1B illustrates a cross-sectional view of an embodiment of a capsule drug package of the present invention after assembly. Small tube 120 is positioned within large tubing 110 so that drug pellet 130 (e.g., sealed dry pellet 130) is positioned within both of the tubes 110 and 120. The sealed dry pellet 130 may be removed by breaking (e.g., piercing) foil covers 112 or 122. In implementations where assembly 100 is utilized in a medical device, the medical device may include additional features (e.g., an advancement assembly) to dislodge and/or remove sealed dry pellet 130 from assembly 100. In particular embodiments, the foil covers 112 and 122 can be configured to be pierced by such an advancement assembly, for example a shaft.

With reference to FIG. 1A, small tubing 120 includes features, such as flared end 121, which enable formation of the interference fit between large tubing 110 and small tube 120. As small tubing 120 slides into large tubing 110, small tubing 120 contacts large tubing 110 over a predetermined length of flared end 121. When small tube 120 slides fully into large tubing 120, the end of small tube 120 covered by foil cover 122 forms an interference fit with large tubing 110. This enables small tube 120 to rest within large tubing 110 and isolates the sealed dry pellet 130 from the outside, by foil covers 112 and 122. In implementations, small tube 120 may be further sealed within large tubing 110 by use of other substances or elements such as glues and various joining elements known in the arts. For example, a glue, such as epoxy, may be used to permanently seal small tube 120 within large tubing 110 after formation of the interference fit.

Bonding Techniques

With reference now to FIGS. 1A and 1B, a variety of bonding techniques are contemplated for attaching pierceable membranes such as foil covers 112 and 122 to their respective tubings 110 and 120. Such techniques include ultrasonic welding, laser welding, and thermal diffusion welding.

In various implementations, tubings 110 and 120 may be commercially cut tubes. Embodiments recognize that commercially cut tubes may have various surface irregularities. Examples of such irregularities include end surface roughness, out of plane end surface and non-parallel cut ends. In practice, the use of tubes having such surface irregularities can significantly elevate the cost of manufacturing the packaging and may negatively affect the bonding between the tubing and respective foil cover. Furthermore, the creation of tubes with precision-cut surfaces significantly raises the cost and difficulty of constructing the packaging.

Accordingly, various embodiments of the invention contemplate the creation of a seal between an end of the tubes and the pierceable membrane by use of a compliant material applied to one or both of the tube and the membrane that applies pressure during the bonding process. In particular embodiments, the compliant material may be formed into a structure comprising a high temperature compliant material which is utilized to create a seal between the end of the tube and the corresponding cover. An example of such a high temperature compliant material is a graphite gasket.

While having benefits, the use of the compliant material may negatively affect the biocompatibility of one or more elements of the packaging. For example, use of a graphite gasket may leave particulate matter on the pierceable membrane. To prevent the graphite gasket from leaving particulate, embodiments of the invention contemplate either a polyimide sheet or stainless-steel sheet or both may be placed between the graphite gasket and the foil.

Figure 2:
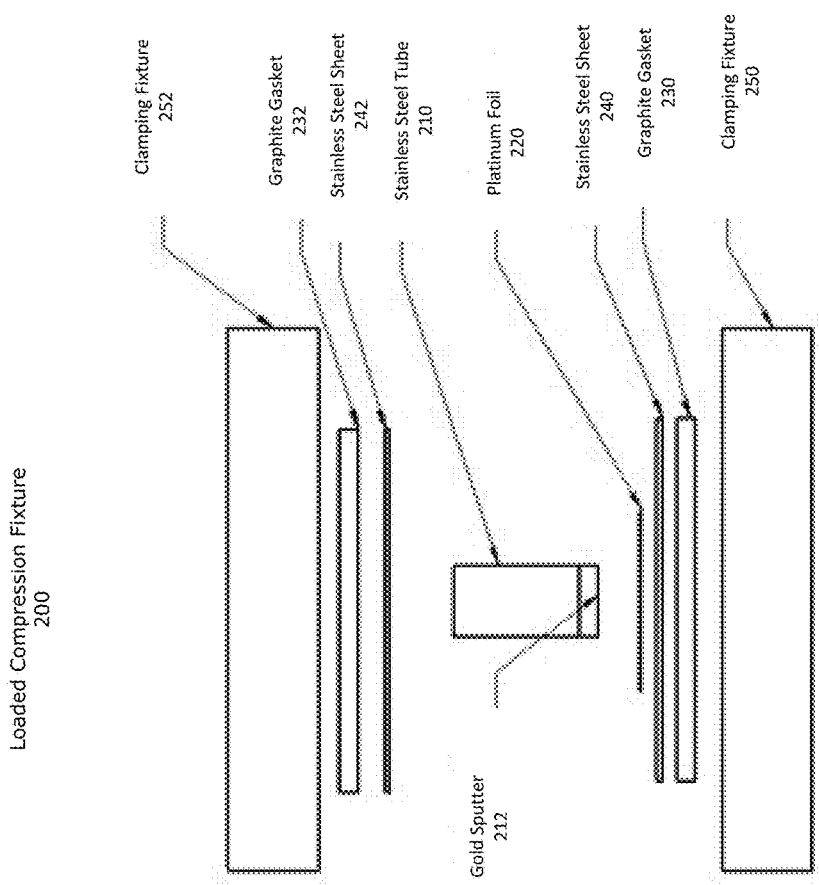
FIG. 2 illustrates a cross-sectional view of a tube for use in a capsule drug package, according to an embodiment.

FIG. 2 illustrates a cross-sectional view of a tube for use in a capsule drug package, according to an embodiment. Such an arrangement as illustrated in FIG. 2 may be used to form the foil-covered tubes 112 and 122 illustrated in FIGS.

1A and 1B. In the example of FIG. 2, loaded compression fixture 200 includes a tubing (stainless steel tube 210) which is positioned in clamping fixtures 250, 252 to be bonded with pierceable membrane 220 (platinum foil 220) by thermal diffusion welding. Stainless steel sheets 240 and 242 are positioned between platinum foil 220 and graphite gasket 230, as well as between stainless steel tube 210 and graphite gasket 232, to prevent graphite particulates from contaminating stainless steel tube 210 and platinum foil 220.

As discussed above, in one or more embodiments, thermal diffusion welding may be used to join the foil to the end of the tube. In an embodiment, one of the openings in stainless steel tube 210 is coated with a substance and then bonded, via thermal diffusion welding with the foil. Other bonding methods known in the art are also contemplated. Preferred embodiments of materials for use in thermal diffusion welding include gold or a gold alloy. Such selection is due to the relatively low processing temperature and/or the melting point of gold and gold alloys as well as many other biocompatible metals. Other metals with low processing temperatures with respect to the melting point of most biocompatible metals may be used. According to one embodiment, in which the thermal diffusion welding is performed using gold or gold alloy, the tube is sputter cleaned with titanium and then sputter coated with gold on the end of the tube for bonding to the foil.

In the example of FIG. 2, the opening of stainless steel tube 210 which is to be bonded with platinum foil 220 is at least substantially coated with gold sputter 212. While in the embodiment of FIG. 2 the stainless-steel tube 210 has been coated via sputtering, other processes to produce a well adhered metal coating are equally suitable e.g., use of other sputter coatings or plasmas coatings.

In various embodiments, the medication element is accessible or removable from the drug capsule via piercing (or a like process) of at least one of the covered tubing ends. In particular embodiments, the assembled drug capsules can be configured to be stored or otherwise placed in an implantable drug delivery device configured to deliver the medication element within the capsule to a selected delivery site such as the heart, brain, GI organ, vein, artery and the like. In these and related embodiments, the drug capsule can be configured to be engaged by a mechanism or the like which pierces the drug capsule and advances the medication element out of the capsule and to a selected delivery site in the body e.g. the brain. According to one or more embodiments, the mechanism may include a piercing and advancement means which both pierces the capsule and advances the medication element out of the capsule to the selected delivery site. In particular embodiments, the piercing and advancement means may correspond to one or more of a metal wire, plastic tube and the like. The piercing and advancement means may also correspond to the use of hydraulic or pneumatic pressure and/or pressure delivering device which is configured to provide hydraulic and/or pneumatic pressure which pierces the capsule and advances the medication element out of the capsule. Further description of an implanted device configured to deliver medication elements, including one which includes a mechanism which pierces the drug capsule or other drug packaging and advances the medication element out of the capsule to selected tissue site may be found in U.S. patent application Ser. Nos. 12/661,767, 12/661,774, 13/645,344, 13/681,825 and 13/684,118 which are incorporated by reference herein for all purposes.

As described herein, various embodiments of the invention contemplate drug packaging (e.g., hermetically sealed drug packaging) and a drug packaging sealing process in which the bioactivity of the drug is preserved by keeping the sealing temperature below that which causes degradation of the particular drug or other therapeutic agent. In particular embodiments, at least about 90%, more preferably at least about 95% and still more preferably at least about 99% of the bioactivity of the drug or other therapeutic agent is preserved after the sealing process by means of keeping the sealing temperature of the capsule in the range of room temperature e.g. about 20 to 26° C. The bioactivity of the selected drug may be tested using pharmacological test methods known in the art such as various antibody and other immunological test methods, one example of such a test method being Enzyme-linked immunosorbent assay or ELISA. In these and related embodiments, an antibody may be obtained which has an epitope which directly or indirectly attaches to an antigen of a bioactive form of the selected therapeutic compound. Also in particular embodiments, the thermal degradation temperature of known therapeutics compounds (e.g. insulin, various integrins and other glucose regulating compounds, furosemide and other anti-seizure medications, flecainide, atropine and other anti-arrhythmic medications) may be ascertained and used to maintain the sealing temperature below that temperature so as preserve a selected bioactivity of the selected drug. According to one or more embodiments, this may be done using the Arrhenius equation or other like equations known in the chemical and reaction kinetics arts. In alternative or additional embodiments, temperature sensitive tablets (having temperature reactive colorings known in the arts) may be positioned in test capsules and used to monitor the temperature inside a fixed number of test capsules during the sealing process. The temperature sensitive tablets and their particular temperature color reactivity, may be selected depending upon the thermal degradation temperature of the particular drug or other therapeutic agent to be packaged. Other temperature sensitive articles are also considered such as various temperature sensitive strips which change color or otherwise undergo a physical or colorometric transformation during a temperature change.

FIGS. 3A and 3B illustrate tubing for use in a capsule drug package, according to an embodiment. With reference to FIG. 3A, tube 310 includes a lumen through which medication (e.g., solid drug pellets) may pass. Tube 310 may have irregularities which impede the attachment of a pierceable membrane to the tube. For example, in the embodiment of FIG. 3B, illustrating a side view of tube 310, irregular end surfaces 320 may hinder the attachment. To overcome difficulties created by such tubular irregularities, bonding techniques (e.g., gold sputter with thermal diffusion welding) may be used to join the membrane and tube.

Figure 3:
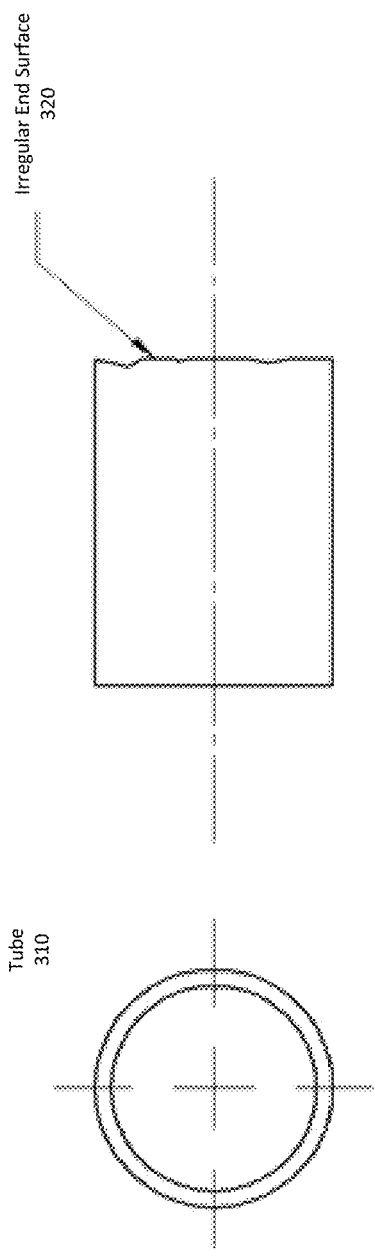
FIGS. 3A and 3B illustrate tubing for use in a capsule drug package, according to an embodiment.
Figure 4:
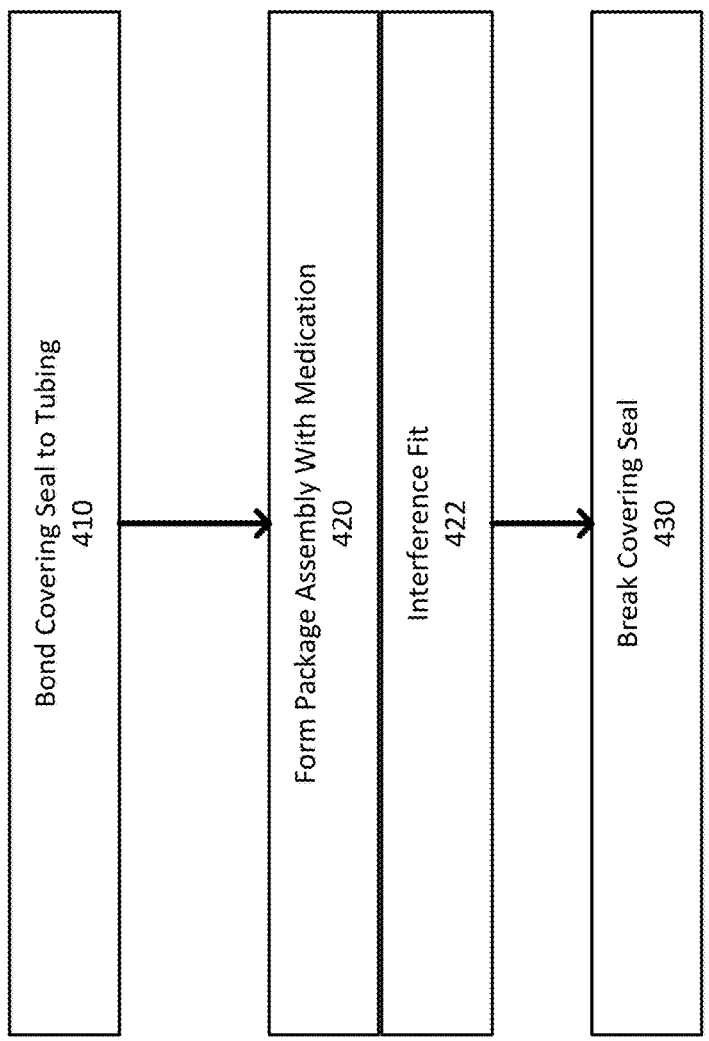
FIG. 4 illustrates a method for assembling and using a capsule drug package of the present invention, according to an embodiment.

FIG. 4 illustrates a method for assembling and using a capsule drug package of the present invention, according to an embodiment. The drug capsule packaging and tubing described with respect to FIG. 1A-1B, FIG. 2, and FIG. 3A-3B may be used with the embodiment of FIG. 4, and reference is made thereof to parts and features of those drawings.

According to one embodiment, a breakable seal (e.g., foil covers 112 or 122) is bonded with tubing (e.g., tubings 110 or 120) to cover one end of the tubing (410). The bonded tubing is then joined with another bonded tubing having a smaller diameter opening to form a package assembly (420) by an interference fit (422). The smaller diameter bonded tubing may have other aspects or features (herein interference fit promoting features), such as a flared shape over a predetermined length, which enables the interference fit to form. Other interference promoting features are also contemplated such as the use of a layer or jacket (now shown) positioned over the smaller diameter tube. Desirably, the layer or jacket comprises a resiliently compressible material (e.g. a polymer) which compresses when it is slid into the opening of the larger tubing and in turn exerts an outward force on the opening of the larger tubing. A drug is stored within the package assembly and isolated from the outside ambient environment at least substantially by the interference fit. When the drug is to be delivered, at least one of the breakable seals is broken (430).

In an example according to FIG. 3, a capsule drug package was assembled by preparing stainless steel tubes. Gold foil was bonded with stainless steel tubes by sputtering gold coating at 400° C. for several hours. The tubes were checked for a hermetic seal with the foil attached. Packaging assemblies were formed by fitting tube-foil assembles into each other. Epoxy was used to seal the packaging assemblies.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the apparatus can be adapted for used in various pediatric and neonatal applications (e.g. by being made smaller and/or changes in shape) as well as any number of veterinary applications including, for example, various canine, feline, bovine and equine application.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Hence, the scope of the present invention is not limited to the specifics of the described embodiments, but is instead limited solely by the appended claims.

What is claimed is:

1. A method for fabricating a packaging for solid medication, the method comprising:
   sliding a first larger diameter tube, the first larger diameter tube having a covered end and an open opposite end, over a first open end of a second smaller diameter tube, the second smaller diameter tube having a flared covered end opposite the first open end, each tube having (i) a lumen, the lumen of either the first larger diameter tube or the second smaller diameter tube including a medication element, and (ii) a covering over their respective covered ends comprising a pierceable material, the pierceable material forming a bond with at least one of the covered end or the flared covered end during a bonding process; wherein the bonding process utilizes a compliant material in conjunction with a compressive force to create the bond; and
   advancing the first larger diameter tube over the flared covered end of the second smaller diameter tube to join and create a hermetic seal between the first larger diameter tube and the second smaller diameter tube by an interference fit between the tubes, wherein the hermetic seal is created by the interference fit alone without a need for elevated temperature to form the hermetic seal.

2. The method of claim 1, wherein the medication element is accessible or removable by piercing at least one of the covered ends.

3. The method of claim 1, wherein the medication element comprises a therapeutic agent which loses bioactivity when exposed to an elevated temperature.

4. The method of claim 3, wherein at least 90% of the bioactivity of the therapeutic agent is preserved.

5. The method of claim 1, wherein the medication element comprises a therapeutic agent for treating epilepsy.

6. The method of claim 5, wherein the therapeutic agent comprises furosemide.

7. The method of claim 1, wherein the pierceable material comprises a metal foil.

8. The method of claim 7, wherein the metal foil comprises gold, platinum, titanium, tantalum or stainless steel.

9. The method of claim 1, wherein the pierceable material comprises a polymeric material.

10. The method of claim 9, wherein the polymeric material comprises polyimide, polyamides or polyethylene terephalate.

11. The method of claim 1, wherein the compliant material comprises a graphite gasket.

12. A hermetically sealed packaging for solid medication comprising a therapeutic agent, the packaging comprising:
    a first larger diameter tube having a covered end and an open opposite end;
    a second smaller diameter tube having a first open end and a flared covered end opposite the first open end;
    wherein each tube includes (i) a lumen, the lumen of either the first larger diameter tube or the second smaller diameter tube including a medication element, and (ii) a covering over their respective covered ends comprising a pierceable material, the pierceable material forming a compressive bond with at least one of the covered end or the flared covered end during a bonding process; and
    wherein the first larger diameter tube and the second smaller diameter tube are joined to form a hermetic seal between the between the first larger diameter tube and the second smaller diameter tube by an interference fit between the tubes, the hermetic seal being created by the interference fit alone without a need for elevated temperature to form the hermetic seal.

13. The packaging of claim 12, wherein the medication element is accessible or removable by piercing at least one of the covered ends.

14. The packaging of claim 12, wherein the therapeutic agent loses bioactivity when exposed to an elevated temperature.

15. The packaging of claim 14, wherein at least 90% of the bioactivity of the therapeutic agent is preserved.

16. The packaging of claim 12, wherein the medication element comprises a therapeutic agent for treating epilepsy.

17. The packaging of claim 16, wherein the therapeutic agent comprises furosemide.

18. The packaging of claim 12, wherein the pierceable material comprises a metal foil.

19. The packaging of claim 12, wherein the pierceable material comprises a polymeric material.

20. The packaging of claim 12, wherein the bonding process utilizes a compliant material in conjunction with a compressive force to create the bond.

21. The packaging of claim 20, wherein the compliant material comprises a graphite gasket.

\* \* \* \* \*